US012152968B2

(12) United States Patent
Harshman et al.

(10) Patent No.: US 12,152,968 B2
(45) Date of Patent: Nov. 26, 2024

(54) BREATH SAMPLE DEVICE INCLUDING FLOW REGULATION DEVICE FOR VOLATILE AND SEMI-VOLATILE SAMPLING

(71) Applicant: Government of the United States, as represented by the Secretary of the Air Force, Wright-Patterson AFB, OH (US)

(72) Inventors: Sean Harshman, Fairborn, OH (US); Mark Hawkins, Tipp City, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 281 days.

(21) Appl. No.: 17/839,524

(22) Filed: Jun. 14, 2022

(65) Prior Publication Data
US 2023/0009301 A1    Jan. 12, 2023

Related U.S. Application Data

(60) Provisional application No. 63/220,606, filed on Jul. 12, 2021.

(51) Int. Cl.
*G01N 1/24*    (2006.01)
*G01N 1/22*    (2006.01)

(52) U.S. Cl.
CPC ....... *G01N 1/24* (2013.01); *G01N 2001/2244* (2013.01); *G01N 2001/248* (2013.01)

(58) Field of Classification Search
None
See application file for complete search history.

(56) References Cited

U.S. PATENT DOCUMENTS 7,063,667 B1 *   6/2006   Ben-Oren ............ A61B 5/0836
                                                  73/23.3
7,153,272 B2 *   12/2006  Talton ................. G01N 33/497
                                                  600/543

(Continued)

FOREIGN PATENT DOCUMENTS

| WO | 2014/132077 A1 | 9/2014 |
| WO | 2017/180606 A1 | 10/2017 |
| WO | 2017/189546 A1 | 11/2017 |

OTHER PUBLICATIONS

Sean W. Harshman, et al., The Identification of Hypoxia Biomarkers From Exhaled Breath Under Normobaric Conditions, Journal of Breath Research, Oct. 28, 2015, 9 (4), IOP Publishing, Bristol, UK.

(Continued)

*Primary Examiner* — Brandi N Hopkins
*Assistant Examiner* — Nigel H Plumb
(74) *Attorney, Agent, or Firm* — AFMCLO/JAZ; Jeffrey V. Bamber

(57) ABSTRACT

A flow regulation device for volatile and semi-volatile sampling onto adsorbent media is provided. The flow regulation device includes a housing having an inlet, an outlet, a secondary inlet that is open to the ambient, a real time flow meter, a controller in electronic communication with the flow meter, and a three-way valve. Gas is drawn through the adsorbent media, into the inlet, and then to the outlet by a vacuum source joined to the outlet. The controller is configured to: (1) actuate the three-way valve to put the vacuum source in-line with the inlet; (2) continuously monitor the flow of gas through the inlet and calculate the time necessary to sample a pre-set volume of gas; and (3) after the pre-set volume of gas passes through the inlet, actuate the three-way valve to put the vacuum source in-line with the secondary inlet.

17 Claims, 5 Drawing Sheets

(56) References Cited

U.S. PATENT DOCUMENTS

2008/0038154 A1* 2/2008 Longbottom ........ G01N 33/497
600/300
2019/0120821 A1* 4/2019 Atsalakis ............... A61B 5/087

OTHER PUBLICATIONS

Sean W. Harshman, et al., Exhaled Isoprene for Monitoring Recovery From Acute Hypoxic Stress, Journal of Breath Research, Nov. 30, 2017, 11 (4), IOP Publishing, Bristol, UK.

Sean W. Harshman, et al., Characterization of Standardized Breath Sampling for Off-Line Field Use, Journal of Breath Research, Dec. 16, 2019, 14 (1), IOP Publishing, Bristol, UK.

Bradley Chew, et al., A low cost, easy-to-assemble, open-source modular mobile sampler design for thermal desorption analysis of breath and environmental VOCs, Journal of Breath Research, May 26, 2022, 16 (3), IOP Publishing, Bristol, UK.

* cited by examiner

BREATH SAMPLE DEVICE INCLUDING FLOW REGULATION DEVICE FOR VOLATILE AND SEMI-VOLATILE SAMPLING Pursuant to 37 C.F.R. § 1.78(a)(4), this application claims the benefit of and priority to prior filed Provisional Application Ser. No. 63/220,606, filed Jul. 12, 2021, which is expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to sampling devices and, more particularly, to a flow regulation device for volatile and semi-volatile sampling onto adsorbent media.

BACKGROUND OF THE INVENTION

Hypoxia-like incidents in aircraft flight have increased over the past decade causing severe safety concerns across the aviation community. The need to monitor flight crews for hypoxic conditions is paramount for continued aeronautical safety. The presence of hypoxic conditions can be determined by measuring certain volatile organic compounds (VOC's) in the flight crew member's exhaled breath.

One of the ways of monitoring flight crews for hypoxic conditions is to have the flight crew members breathe into an air tight container, such as an exhaled breath bag upon landing the aircraft. The breath bag can then be connected to a thermal desorption tube containing adsorbent media therein. One end of the thermal desorption tube is connected to the breath bag, and the other end of the tube is connected to a gas detector having a flow rate calibrated vacuum pump associated therewith. Such sampling requires an accurate volume of gas to be drawn through the adsorbent media tube.

Previous volatile transfer methods require personnel to calibrate the vacuum pump's flow rate using a "representative" adsorbent material to determine an appropriate sampling time to achieve a specific volume of gas. Following the calibration of the pump, personnel physically connect the container, the adsorbent material, and run the pump for a specific period of time to generate a specific volume of material sampled. This process, however, is reliant on steps that are prone to error. First, the flow rate calibration for the pump assumes uniform composition of sampling media, which is a poor assumption (due to differences in tube loading of adsorbent material). Second, personnel are required to manually time and disconnect components to initiate and terminate sampling. Third, personnel are required to perform calculations to determine the volume of air based on the air flow through the pump and time the pump is run.

An alternative potential solution would be to use a dosing controller with a vacuum pump. Some commercially available products, such as an Alicat Scientific, Inc. flow controller with a totalizer function, use the combination of a mass flow meter with a 2-way or proportional valve to perform a similar function. The main disadvantage of this method is the stoppage of flow to any follow-on sensors and the vacuum pump when the desired dose is reached. The large pressure swings caused by this configuration can cause faults in sensor and pump performance.

Therefore, a need exists for a more accurate means of sampling volumes, independent of changes in sampling media, personnel, and sampling environment.

SUMMARY OF THE INVENTION

The present invention relates generally to sampling devices and, more particularly, to a flow regulation device for volatile and semi-volatile sampling onto adsorbent media.

While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a flow regulation device for volatile and semi-volatile sampling onto adsorbent material contained in a tube is provided. The flow regulation device comprises a housing having a plurality of openings therein, and a gas inlet extending into a first opening in the housing for admitting gas into the housing. The inlet is used for establishing a connection with the adsorbent material-containing tube. The flow regulation device has an outlet for releasing gas outside the housing through a second opening in the housing. The outlet is in fluid communication with the gas inlet or a secondary inlet, and is usable for establishing fluid communication with a vacuum source. A real time flow meter is located in the housing. The flow meter is in fluid communication with the inlet. The flow regulation device further comprises a three-way valve having three branches comprising: a first branch in fluid communication with the gas inlet; the second branch in fluid communication with the outlet; and a third branch for drawing air through a secondary inlet from the ambient surroundings. The flow regulation device also comprises a controller, such as a control circuit board in electronic communication with the flow meter.

The controller is configured to: (1) actuate the three-way valve to put the vacuum source in-line with the inlet; (2) continuously monitor the flow of gas through the inlet and calculate the time necessary to sample a pre-set volume of gas; and (3) after the pre-set volume of gas passes through the inlet, actuate the three-way valve to put the vacuum source in-line with the secondary inlet.

The vacuum source can be any suitable type of vacuum source including, but not limited to a vacuum pump or a container having gas therein at less than ambient (e.g., less than atmospheric) pressure. In other embodiments, instead of drawing a vacuum with a vacuum source that is in fluid communication with the outlet, a positive gas pressure source can be placed in fluid communication with the inlet. In the latter case, the adsorbent material-containing tube can be placed between the positive gas pressure source and the inlet.

The present invention, therefore, provides a real-time flow rate sensor with a divert valve to provide accurate sampling of specific volumes without user input, eliminating the sources of sampling error of the prior practice.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity of illustration.

DETAILED DESCRIPTION OF THE INVENTION

The present invention relates generally to sampling devices and, more particularly, to a flow regulation device for volatile and semi-volatile sampling onto adsorbent media. The phrase "at least semi-volatile", as used herein, includes both semi-volatile and volatile materials.

Figure 1:
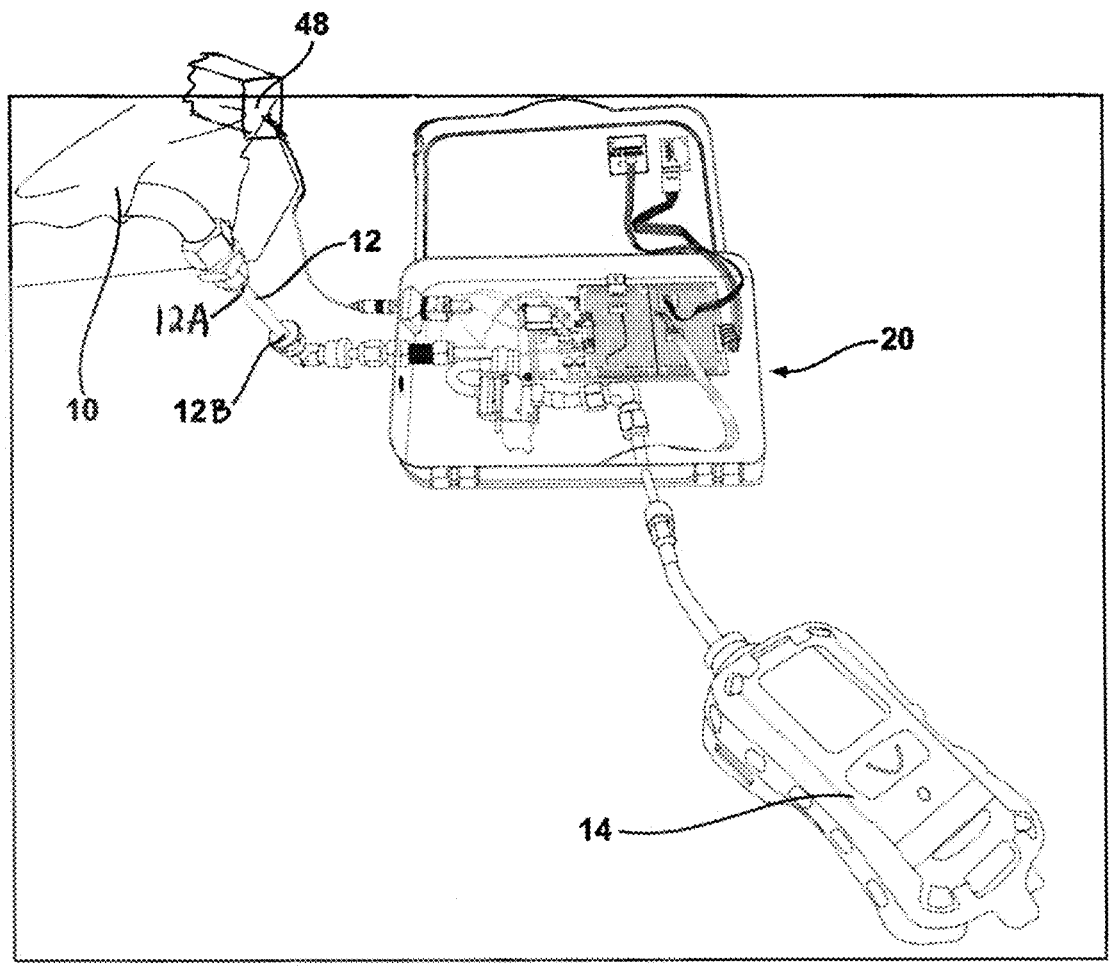
FIG. 1 is a perspective view of the flow regulation device being used to regulate the flow of gas from a breath bag through an adsorbent material-containing tube.

FIG. 1 shows one non-limiting embodiment of the flow regulation device 20 in context for use. As shown in FIG. 1, the flow regulation device 20 is used with a source of gas, which may be in the form of a volatile material container such as a breath bag 10, an adsorbent material tube 12, and a vacuum source such as a vacuum pump 14. The adsorbent material tube 12 has a first end 12A, a second end 12B, and an interior with adsorbent material therein. The breath bag 10 is connected to the first end 12A of the adsorbent material tube 12. The second end 12B of the adsorbent material tube 12 is connected to the flow regulation device 20. The breath bag 10 and the adsorbent material tube 12 are in fluid communication with each other, and the breath bag 10 is in fluid communication with the flow regulation device 20. The vacuum pump 14 is joined to the flow regulation device 20 to draw gas from the breath bag 10 through the flow regulation device 20. The term "fluid communication", as used herein, means that gas can flow between the joined components.

The volatile material container 10 can comprise any suitable type of closed container. The container is closed with the exception of an opening provided for collecting gas therein (and for removing the gas with the flow regulation device 20). Suitable containers include, but are not limited to 1 liter ALTEF® polypropylene bags supplied by Jensen Inert Products, Coral Springs, FL, and TEDLAR® sample bags available from SKC, Inc. of Eighty Four, PA.

The adsorbent material tube 12 has an interior and an opening at each end. The adsorbent material is contained in the interior of the tube. The adsorbent material tube 12 can comprise any suitable type of adsorbent material tube including, but not limited to stainless steel TENAX TA thermal desorption (TD) tubes supplied by Markes International, South Wales, Uk.

The vacuum source can be a vacuum pump or a container containing gas at less than atmospheric pressure. If a vacuum pump is used, the vacuum pump 14 can be any suitable type of pump capable of pumping (or drawing) air and other gases by vacuum including, but not limited to a Honeywell MultiRAE Pro pump supplied by RAE Systems, Inc., San Jose, CA. The vacuum pump 14 can be run at any suitable flow rate up to the maximum value of the flow sensor including, but not limited to about 270 ml/min. Unless specifically claimed, the volatile material container 10, the adsorbent material tube 12, and the pump 14 will not comprise part of the flow regulation device 20. If the vacuum source comprises a container containing gas at less than atmospheric pressure, it may be referred to as an "at least partially evacuated container".

Figure 2:
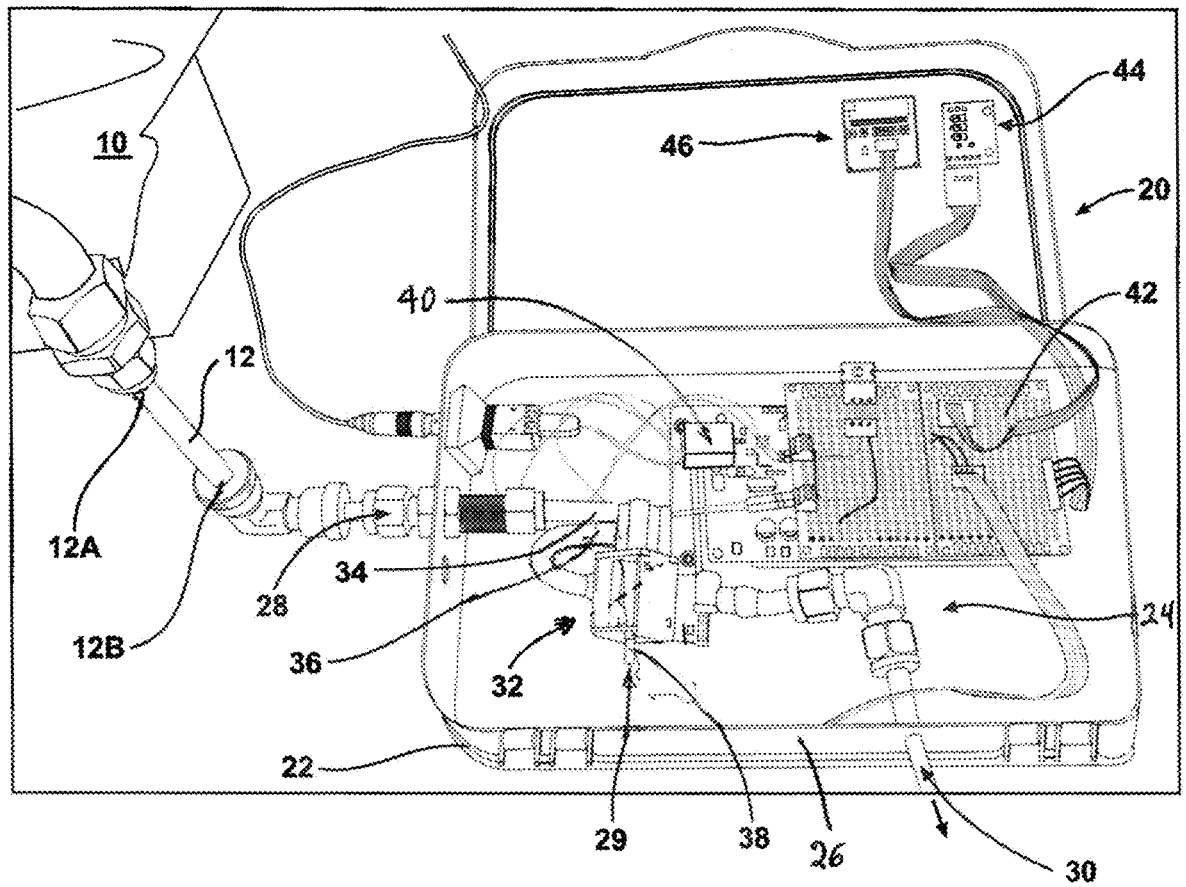
FIG. 2 is an enlarged perspective view of the flow regulation device.

FIG. 2 shows that the flow regulation device 20 generally comprises: a housing 22 having an interior 24, an exterior surface 26, an opening for a gas inlet (or "inlet") 28, and an opening for a gas outlet (or "outlet") 30; a three-way valve 32; a real-time flow meter (or "flow sensor") 40; and a controller 42. The gas inlet 28 extends into the opening in the housing for admitting gas into the housing 22. The outlet 30 is for releasing gas outside the housing 22. The outlet 30 is in fluid communication with the inlet 28 when the three-way valve 32 is set to permit gas to be drawn into the inlet 28. The flow regulation device 20 may be configured to only permit gas to be drawn inward from a source into one of the inlet 28 or a secondary inlet. In such case, gas is unable to flow back to the source.

The three-way valve 32 comprises three branches comprising: a first branch 34 in fluid communication with the gas inlet 28; a second branch 36 in fluid communication with the outlet 30; and a third branch 38 for drawing air through a secondary inlet 29 from the ambient surroundings. The secondary inlet 29 may have an open end that is located outside the housing 22; or, it may be located inside of the housing 22 (provided that the housing has at least one opening therein for air to enter the housing). In the embodiment shown in the drawings, the opening of the secondary inlet 29 is located inside the housing 22. Depending on how the valve 32 is set, either the first branch 34, or the third branch 38 (with the secondary inlet) will be in fluid communication with the second branch 36 and the outlet 30. If gas is drawn through the gas inlet 28, it will pass through the first branch 34 and be discharged out of the outlet 30. This may be referred to as the primary pathway. If air is drawn through the secondary inlet 29, it will pass through the second branch 36 and be discharged out of the outlet 30. This may be referred to as the secondary pathway.

Figure 2A:
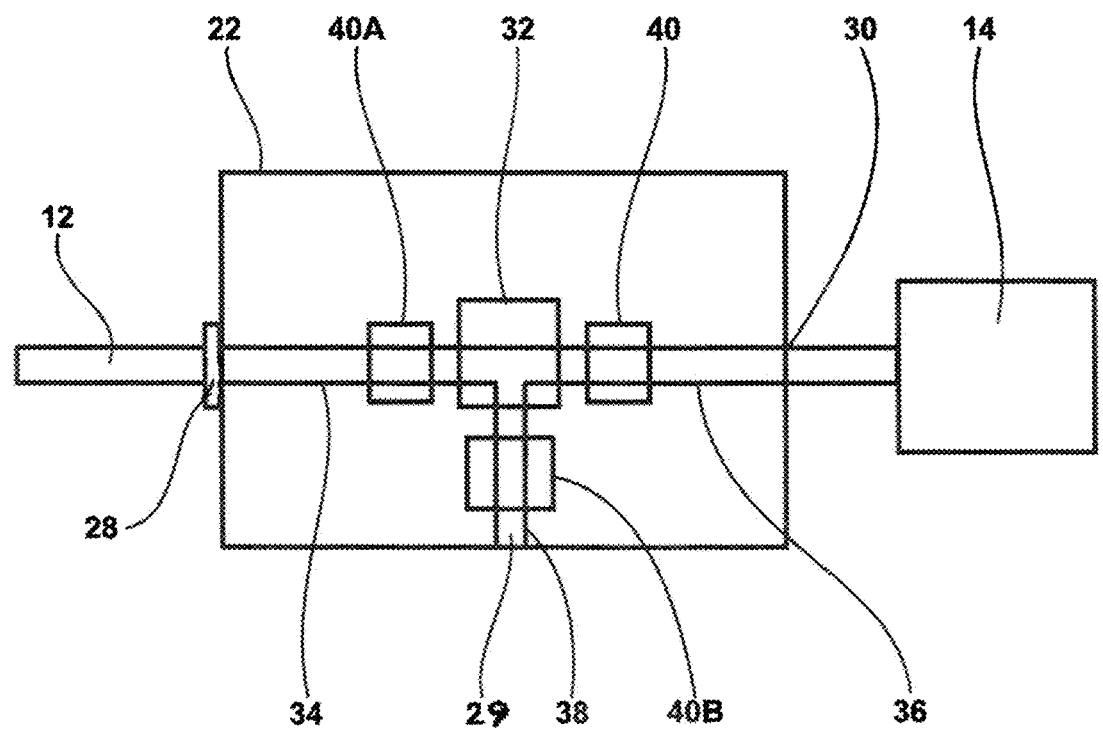
FIG. 2A is a schematic view of a flow regulation device showing various possible locations for a flow meter.

The flow meter (or "flow sensor") 40 may be located in the housing 22. The flow meter 40 is in fluid communication with the three-way valve 32. The flow meter 40 can comprise any suitable type of flow meter. The flow meter 40 may be located such that gas flows into the gas inlet 28 or into the secondary inlet 29, through either the first 34 or third 38 branches of the three-way valve 32 respectively, through the flow meter 40, and through the second branch 36 of the three-way valve 32 to the pump 14. As shown in FIG. 2A, it is also possible to locate the flow meter 40A in the primary pathway so that it only measures gas passing through the inlet 28 into the first branch 34, and does not measure air drawn into the secondary inlet 29. Alternatively, it is also possible to locate the flow meter 40B so that it is only in line with the secondary path.

The controller 42 may be a circuit board (which may be a microcontroller) that carries out the data processing of the device, such as receiving the measurements from the flow meter 40 and controlling the operation of the three-way valve 32. The controller (control circuit board) 42 is operatively connected to the flow meter 40. The control circuit board 42 is configured to: (1) actuate the three-way valve 32 to put the vacuum source in-line with the inlet 28; (2) continuously monitor the flow of gas from the inlet 28 through the primary pathway and calculate the time necessary to sample a pre-set volume of gas; and (3) after the pre-set volume of gas passes through the primary pathway, actuate the three-way valve 32 to put the vacuum source in-line with the secondary inlet 29 (so that air flows through the secondary pathway).

The input device 44 provides operator input for controlling the operation of the flow regulation device 20. The input device 44 can be any suitable type of input device including, but not limited to mechanical and digital input devices. In the embodiment shown, the input device 44 is a digital device. The input device 44 can be configured to receive any suitable input including, but not limited to: start/stop instructions; and a selection for the volume of gas to be drawn through the flow regulation device 20.

The display 46 can be any suitable type of display device including, but not limited to a digital display. The display 46 can show any suitable information. Such information may include, but is not limited to: the volume of gas drawn through the flow regulation device 20.

The power source 48 can be any suitable type of power source. The flow regulation device 20 may be battery powered or it may be powered by plugging the flow regulation device into an electrical outlet.

The flow regulation device 20 may be used as follows. Prior to initialization of the sampling, the vacuum source 14 is activated (e.g., if it is a pump, it is turned on) with the three-way valve 32 set to allow air to be pulled through the secondary inlet 29 from the ambient surroundings. To initialize the sampling, the three-way valve 32 will be actuated to put the vacuum source 14 in-line with the adsorbent material tube 12 and the source of gas, such as the closed container 10 (or with the surrounding environment if a closed container is not used). The real time flow meter 40 will continuously monitor the flow to calculate the time necessary to sample the preset volume of gas, and will actuate the valve 32 back to a setting where air is drawn from the ambient surroundings (i.e. ending sampling) when the volume is achieved. This allows accurate volumes to be sampled without any physical change in connections, personnel timing, or assumptions of uniformity of adsorbent material.

After the desired quantity of gas is drawn through the tube 12, the tube 12 is then removed from the device 20 and inserted into test equipment for analyzing the volatile material(s) adsorbed onto the adsorbent media within the tube 12. In some cases, this involves placing the tube 12 into a gas chromatograph/mass spectrometer and heating the tube to the desired temperature for releasing VOC's. The VOC's are then measured by the gas chromatograph/mass spectrometer. Exhaled isoprene is of particular emphasis in monitoring for recovery from acute hypoxic stress.

This invention, thus, allows accurate gas transfer from a closed container (e.g., an exhaled breath bag) or the environment onto adsorbent material using a pump independent of personnel, adsorbent variability, and sampling environment. This is directly applied to exhaled breath analysis, but may also be used in any sampling environment that requires accurate volumetric transfer of volatiles from closed containers, or from open sources, such as environmental sampling.

There are numerous, non-limiting embodiments of the invention. All embodiments, even if they are only described as being "embodiments" of the invention, are intended to be non-limiting (that is, there may be other embodiments in addition to these), unless they are expressly described as limiting the scope of the invention. Any of the embodiments described herein can also be combined with any other embodiments in any manner to form still other embodiments.

In some embodiments, albeit less desirable embodiments, it could be possible to eliminate the housing and simply place the other components of the flow regulation device 20 on a surface.

Figure 3:
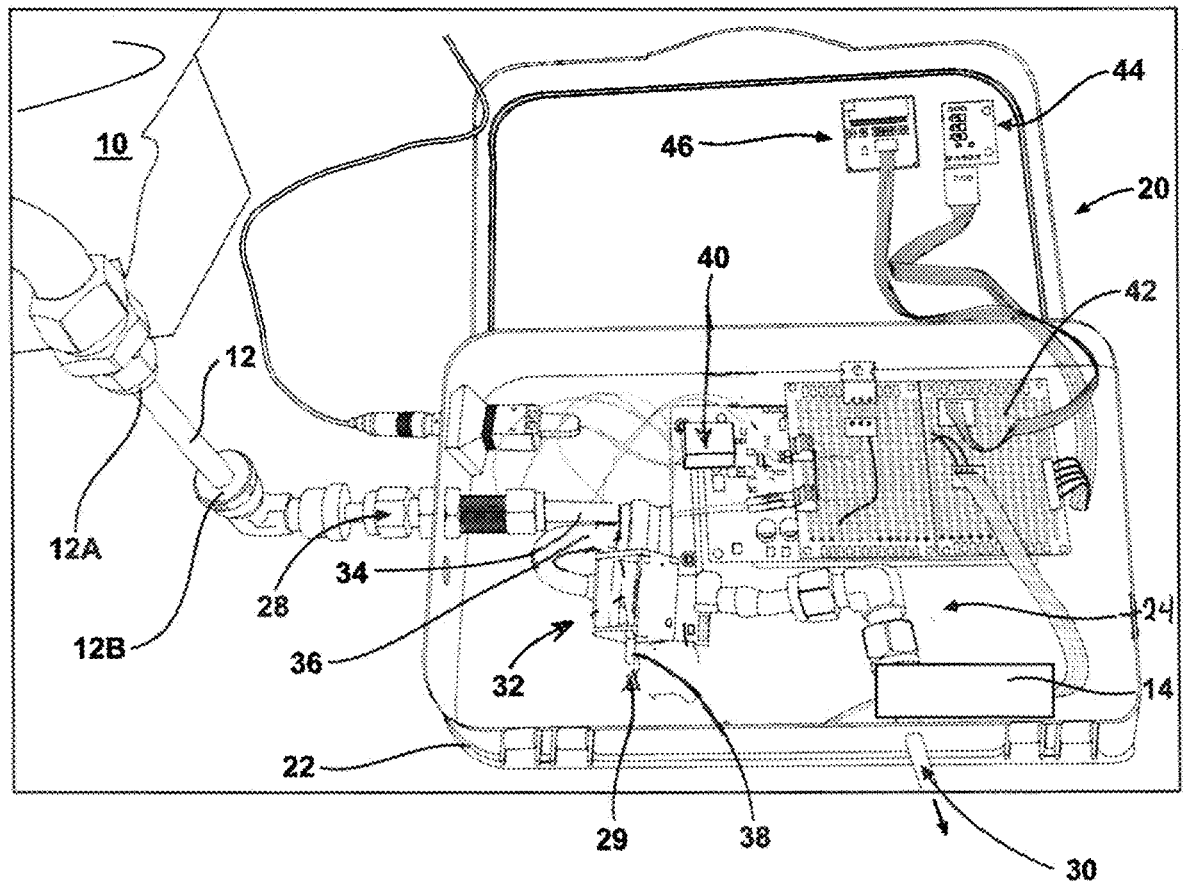
FIG. 3 is a perspective view of a flow regulation device comprising a pump within its housing.

In some embodiments, as shown in FIG. 3, the flow regulation device 20 may comprise a vacuum pump located inside the housing 22. In such a case, the vacuum pump 14 will have a pump inlet that is in fluid communication with the gas inlet 28 and a pump outlet that is in fluid communication with the outlet 30 of the flow regulation device.

Figure 4:
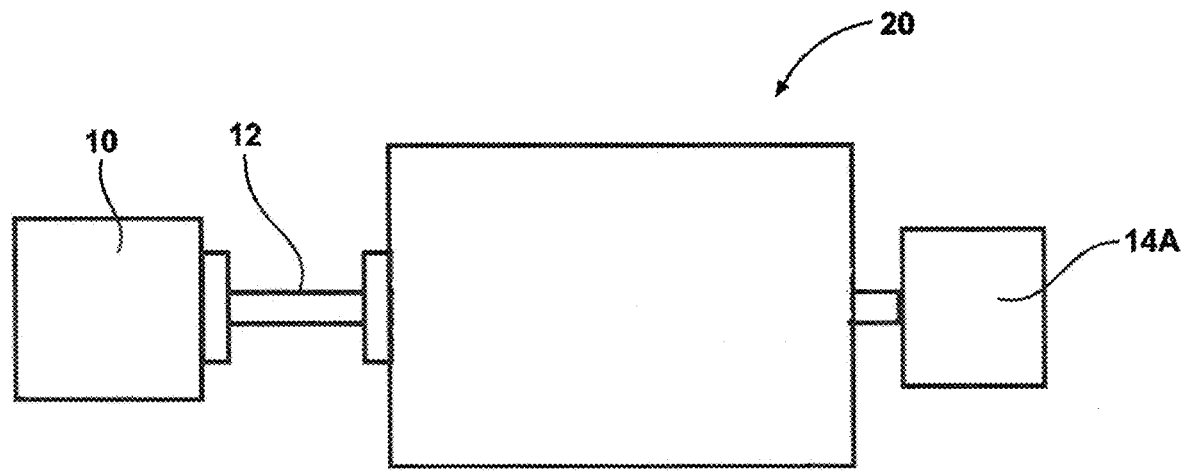
FIG. 4 is a schematic view of a flow regulation device in which gas is drawn through the device by a vacuum container.

FIG. 4 shows that in an alternative configuration, the vacuum source can be provided by connecting a container containing gas at less than atmospheric pressure (such as a Summa canister) 14A to the vacuum port, outlet 30. A Summa canister is a metal canister that is put under at least partial vacuum, and samples are drawn in by opening the canister to the intended sampling source. The equilibration in pressure draws the sample into the canister. In this embodiment, when sampling, the flow would be sent through the collection media (such as an adsorbent material tube). When not sampling, ambient air would be drawn through the third branch 38 of the three-way valve 32.

Figure 5:
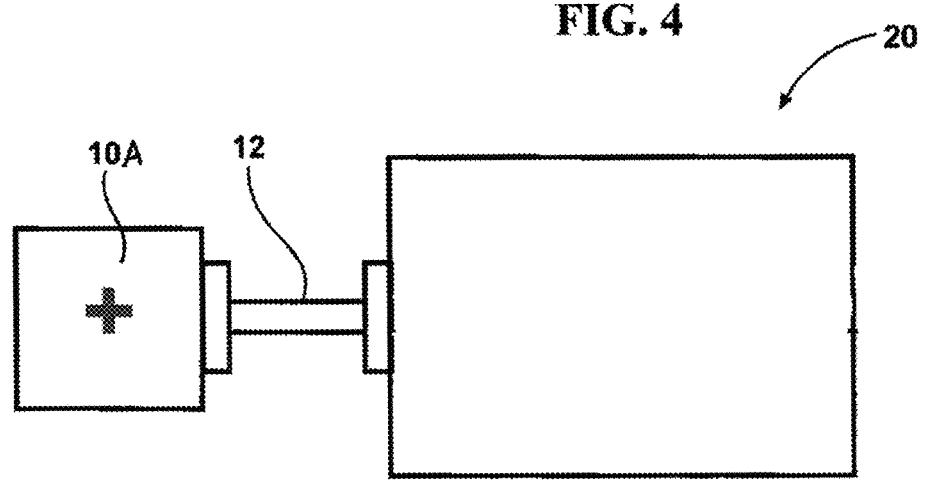
FIG. 5 is a schematic view of a flow regulation device in which gas is forced through the device by a source of positive gas pressure.

FIG. 5 shows that in another alternative configuration, instead of drawing a vacuum with a vacuum source that is in fluid communication with the outlet 30, a positive gas pressure source can be placed in fluid communication with the inlet 28. (In such a case, the volatile material container 10 shown in the drawings can be replaced with the positive gas pressure source 10A.) In some cases, the positive gas pressure source may be a source of exhaust gas. In this case, the adsorbent material-containing tube 12 can be placed between the positive gas pressure source and the inlet 28. In the same way that the flow regulation device 20 configuration avoids stoppage to downstream sensors in the vacuum configuration, this configuration helps to mitigate upstream impacts when collecting from a pressurized source.

Figure 6:
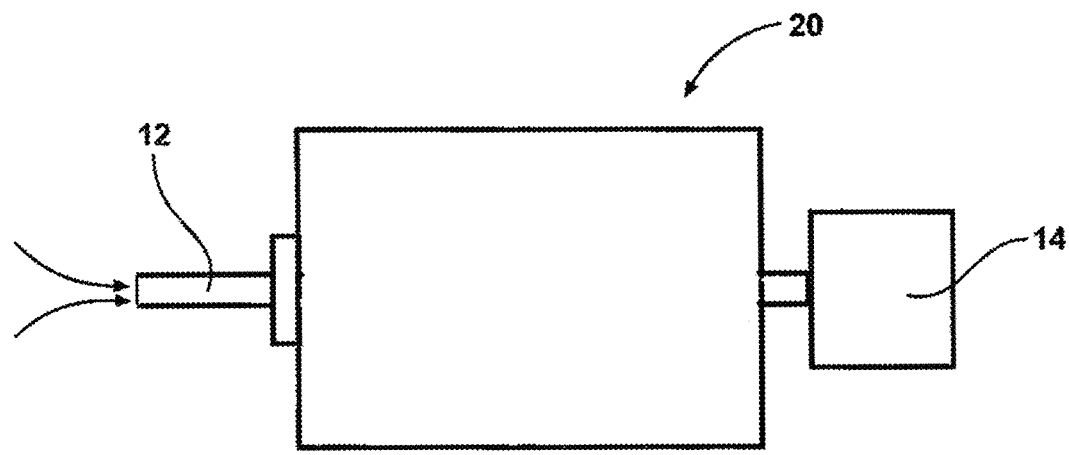
FIG. 6 is a schematic view of a flow regulation device in which an adsorbent material tube is open to the atmosphere for environmental sampling.

While described for closed containers such as exhaled breath bags, environmental samples are routinely sampled in a similar fashion. In such cases, as shown in FIG. 6, instead of air being drawn from a bag through the adsorbent material, the adsorbent material will be open to the surrounding environment.

The flow regulation device 20 may be provided with additional features. Although no other gas sensors are currently required for the primary function of the device 20 (precisely sampling a specific volume from a gas source), additional gas sensors may be included. For example, real-time sensors such as such as $CO_2$ sensors may be integrated into the device 20. In addition, the device 20 may be configured to export functions of the real-time flow rates and any data from integrated sensors. In some cases, the real-time flow rates and data from the sensors may be transmitted to a computer for display on a screen and/or to record and/or print with a printer.

Another improvement comprises the addition of a restrictor to the vent (the third branch 38 of the three-way valve 32). The restrictor can be in the form of an orifice, filter, needle valve, or differential pressure regulator to further reduce flow changes when switching between the normal and sampling states.

The sampling devices described herein can provide a number of advantages. It should be understood, however, that these advantages need not be required unless they are set forth in the appended claims. This invention allows for the accurate sampling of closed containers or the environment into adsorbent material (tubes). As gas loading onto adsorbent material is the basis for normalization of samples in exhaled breath and environmental sampling, accurate volumes are necessary to determine differences among samples. The invention eliminates the requirement to calibrate the pump, time connections, and as a result improves the accuracy of the volatile material transfer. This invention represents a major step forward in sampling by removing the variability associated with adsorbent material, personnel errors, and environmental conditions. The invention also eliminates the large pressure swings and potential faults in sensor and pump performance associated with using a dosing controller with a vacuum pump. By using a three-way valve, the flow is never interrupted, minimizing the impact to downstream components.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined" includes both those configurations in which an element is temporarily joined to another element, or in which an element is permanently joined to another element.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A flow regulation device for sampling at least semi-volatile material onto adsorbent material contained in a tube, said flow regulation device comprising:
    a housing having a plurality of openings therein;
    a gas inlet extending into a first opening in said housing for admitting gas into said housing, said inlet being for establishing a connection with an adsorbent material-containing tube;
    an outlet for releasing gas outside said housing through a second opening in said housing, said outlet being in fluid communication with one of said gas inlet or with a secondary inlet, and being usable for establishing fluid communication with a vacuum source;
    a three-way valve comprising three branches comprising:
        a first branch in fluid communication with said gas inlet;
        a second branch in fluid communication with said outlet; and
        a third branch for drawing air through said secondary inlet from the ambient surroundings;
    a real time flow meter located in said housing, said flow meter being in fluid communication with the three-way valve; and
    a controller in electronic communication with said flow meter, wherein when a vacuum source is connected to the outlet, the controller is configured to: (1) actuate the three-way valve to put the vacuum source in-line with the gas inlet, forming a primary pathway; (2) continuously monitor the flow of gas through the inlet and calculate the time necessary to sample a pre-set volume of gas; and (3) after the pre-set volume of gas passes through the gas inlet, actuate the three-way valve to put the vacuum source in-line with the secondary inlet, forming a secondary pathway.

2. The flow regulation device of claim 1 which is configured to only permit gas to be drawn inward from a source into one of said inlet and said secondary inlet, wherein gas is unable to flow back to said source.

3. The flow regulation device of claim 1 wherein said inlet is configured for removably joining an adsorbent material tube thereto.

4. The flow regulation device of claim 1 wherein said outlet is configured for joining a vacuum source thereto with the vacuum source being located outside of said housing.

5. The flow regulation device of claim 1 wherein said vacuum source is a vacuum pump.

6. The flow regulation device of claim 1 wherein said vacuum source is a container with gas therein at less than atmospheric pressure.

7. The flow regulation device of claim 4 further comprising an adsorbent material tube joined to said inlet and a vacuum source joined to said outlet.

8. The flow regulation device of claim 1 further comprising a vacuum pump located inside said housing, wherein said vacuum pump has a pump inlet that is in fluid communication with said gas inlet and a pump outlet that is in fluid communication with the outlet of the flow regulation device.

9. The flow regulation device of claim 1 wherein the flow meter is located in-line between the three-way valve and the outlet so that said flow meter can measure flow whether it is occurring through the primary pathway or the secondary pathway.

10. The flow regulation device of claim 1 wherein the flow meter is in-line with only the primary pathway.

11. The flow regulation device of claim 1 further comprising a digital display and input operatively connected to said controller.

12. A system for sampling at least semi-volatile material onto adsorbent material contained in a tube, said system comprising:
a) a flow regulation device for sampling at least semi-volatile material onto adsorbent material contained in a tube, said flow regulation device comprising:
   a housing having a plurality of openings therein;
   a gas inlet extending into a first opening in said housing for admitting gas into said housing, said inlet being for establishing a connection with an adsorbent material-containing tube;
   an outlet for releasing gas outside said housing through a second opening in said housing, said outlet being in fluid communication with one of said gas inlet or with a secondary inlet, and being usable for establishing fluid communication with a vacuum source;
   a three-way valve comprising three branches comprising:
      a first branch in fluid communication with said inlet;
      a second branch in fluid communication with said outlet; and
      a third branch for drawing air through a secondary inlet from the ambient surroundings;
   a real time flow meter located in said housing, said flow meter being in fluid communication with the three-way valve; and
   a controller in electronic communication with said flow meter, wherein when a vacuum source is connected to the outlet, the controller is configured to: (1) actuate the three-way valve to put the vacuum source in-line with the gas inlet; (2) continuously monitor the flow of gas through the inlet and calculate the time necessary to sample a pre-set volume of gas; and (3) after the pre-set volume of gas passes through the gas inlet, actuate the three-way valve to put the vacuum source in-line with the secondary inlet;
b) a tube containing adsorbent material, said tube having a first end and a second end, wherein the second end is joined to the gas inlet of said flow regulation device; and
c) a vacuum source in fluid communication with said outlet.

13. The system of claim 12 wherein the first end of said tube is joined to a breath bag containing exhaled human breath.

14. The system of claim 12 wherein the first end of said tube is open to the atmosphere.

15. A method of sampling volatile and semi-volatile materials onto adsorbent material, said method comprising:
a. providing a flow regulation device comprising:
   a housing;
   a gas inlet extending into an opening in said housing for admitting gas into said housing;
   a real time flow meter located in said housing, said flow meter being in fluid communication with said inlet;
   a controller in electronic communication with said flow meter;
   an outlet for releasing gas outside said housing, said outlet being in fluid communication with said inlet; and
   a three-way valve comprising three branches comprising: a first branch in fluid communication with said inlet; a second branch in fluid communication with said outlet; and a third branch for drawing air through a secondary inlet from the ambient surroundings;
b. providing a tube containing adsorbent material, said tube having a first end and a second end;
c. obtaining a container containing gas with at least semi-volatile material therein;
d. placing a vacuum source in fluid communication with the outlet of the flow regulation device;
e. connecting the second end of the tube containing adsorbent material to the gas inlet of said flow regulation device;
f. connecting the container containing gas to the first end of the tube containing adsorbent material;
g. actuating the three-way valve to put the vacuum source in-line with the gas inlet;
h. continuously monitoring, by said controller, the flow of gas through the gas inlet and with said controller calculating the time necessary to sample a pre-set volume of gas; and
i. after the pre-set volume of gas passes through the inlet, actuating, with said controller, the three-way valve to put the vacuum source in-line with the secondary inlet.

16. The method of claim 15 wherein in step d) the outlet is configured for joining a vacuum source thereto with the vacuum source being located outside of said housing.

17. The method of claim 15 wherein in step d), the vacuum source comprises a vacuum pump located inside said housing of said flow regulation device, wherein said vacuum pump has a pump inlet that is in fluid communication with said gas inlet and a pump outlet that is in fluid communication with the outlet of the flow regulation device.

* * * * *